United States Patent [19]
Grippi et al.

[11] Patent Number: 6,074,383
[45] Date of Patent: Jun. 13, 2000

[54] LASER LANCET TIP

[75] Inventors: Nicholas A. Grippi, Ramsey; Alyssa J. Dassa, Wayne; Bradley Wilkinson, Wanaque; Beth Plokhoy, Jefferson, all of N.J.

[73] Assignee: Becton Dickinson and Company, Franklin Lakes, N.J.

[21] Appl. No.: 09/164,096

[22] Filed: Sep. 30, 1998

[51] Int. Cl.[7] .................................................. A61B 18/18
[52] U.S. Cl. .................................. 606/14; 606/2; 606/13; 606/1; 607/88; 607/89; 607/90
[58] Field of Search ................ 606/14, 15, 16, 606/17, 9, 10; 607/87, 88, 89, 90

[56] References Cited

U.S. PATENT DOCUMENTS

| | | | |
|---|---|---|---|
| 5,267,996 | 12/1993 | Fletcher | 606/17 |
| 5,318,023 | 6/1994 | Vari et al. | 606/15 |
| 5,554,153 | 9/1996 | Costello et al. | 606/17 |
| 5,839,446 | 11/1998 | Waner et al. | 606/17 |
| 5,908,416 | 6/1999 | Castello et al. | 606/17 |
| 5,947,957 | 9/1999 | Morris | 606/9 |

*Primary Examiner*—John P. Leubecker
*Assistant Examiner*—Sonya Harris-Ogugua
*Attorney, Agent, or Firm*—Nanette S. Thomas, Esq.

[57] ABSTRACT

A laser lancet tip and method for controlling laser incisions for the purpose of taking blood samples from patients in a variety of body locations and age groups. A removable tip on a laser is used to mask a laser pulse and modify the length and width of an incision made by the laser by only allowing a portion of the laser beam to contact the target surface. The depth of the incision may be controlled by either a lens or filter which is optically aligned with the laser beam.

11 Claims, 2 Drawing Sheets

LASER LANCET TIP

BACKGROUND OF THE INVENTION

1. Field of the Invention

The present invention relates to a medical device for use in taking blood samples. More particularly, the present invention is directed to a laser lancet for use in obtaining precise blood samples from patients.

2. Description of the Related Art

The taking of blood samples is a necessary part of the process of diagnosing and controlling disease. Traditionally, blood samples are obtained by puncturing the skin of a patient's finger with a sharp object such as a needle or pointed blade. Larger samples required the use of a syringe needle which would be inserted into a vein. The needles and pointed blades include exposed points which are a danger to health care workers and produce a significant fear and apprehension in patients who anticipate a painful experience. Once used, the blood infected needles and pointed blades must be discarded under carefully controlled conditions. Moreover, the use of disposable needles and pointed blades requires medical providers to keep a large inventory at all times. The result is an expensive and potentially dangerous process for obtaining blood samples from patients.

Recently, lasers commonly known as laser lancets, have been used as a substitute to a needle or pointed blade for obtaining blood samples from patients. A laser lancet can be used to puncture the surface of the skin causing a rupture of subcutaneous capillaries and the expression of blood or can puncture a hole through the skin and a vein for larger blood samples. The blood can then be collected for analysis. These laser lancets contain complex circuitry and control systems to vary the power, duration, pulse rate, and size of the laser pulses. A small blood sample from the finger can be taken by a single short high power pulse which vaporizes the skin tissue and severs many small blood vessels. This results in a blood sample of a few drops. To collect a larger blood sample, the laser must be able to deliver a greater power pulse or the same power pulse repeated over a short period of time to puncture the skin and an underlying vein. After puncturing the vein a larger volume of blood can be collected. Varying the power, duration, and pulse rate of a laser pulse requires complex circuitry and control systems which greatly increases the cost of the laser lancet and the training needed to operate the laser. This results in increased cost to the patient.

Further, many of the prior art laser lancets are designed to puncture the skin of a finger or a vein in an arm of an adult patient. Infant patients require the puncture to have a larger surface area but less depth than adults to collect the same amount of blood. An infant's capillaries are close to the skin and the depth can, therefore, be reduced. This requires the blood taker to be skilled in varying the size of the puncture depending on the age of the patient. Additionally, even though a laser pulse remains the same, the depth of the puncture will vary depending on the location of the puncture. The skin on an arm is soft and will vaporize easily causing a deeper puncture. The skin of a finger, however, may have callouses or is generally harder, so it is more difficult to vaporize with the laser pulse. The result is more complex circuitry and control systems and, consequently, additional training of personnel. Again, there is increased cost to the patient.

It is well-known in the industry to use a laser system for surface reprofiling in which a mask is disposed between the laser and the target. The mask provides a predefined profile of resistance to laser radiation erosion by selectively absorbing some of the laser radiation while permitting the remainder to be transmitted to the target in accordance with the mask profile. The mask, however, only controls the amount of energy which is incident on the target and does not control the expanse (surface area and depth) of the affected skin.

It is also known to modify the intensity distribution of a laser beam by attaching a rotatable mask which spins and allows only a portion of the laser beam to pass to the target surface. The intensity modifying mask, however, requires a means to rotate the mask and must be structurally connected so it can be rotated. This, of course, increases the complexity and cost of the system. Moreover, the intensity modifying mask does not control the expanse of the incision.

It is therefore desirable to provide a laser lancet assembly which can deliver a pre-determined precisely controlled laser pulse.

SUMMARY OF THE INVENTION

A laser lancet assembly for controlling a blood collection incision is provided by the present invention.

The assembly includes a laser lancet having an end which admits a laser beam for affecting a blood collection incision at a patient site. The assembly further includes a lancet tip selectively positionable over the laser beam admitting end of the laser lancet. The tip includes an elongated housing having an aperture of size and shape to define a controlled pre-selected incision expanse. The aperture thus provides a precise pre-determined incision which is based upon the site in which blood is taken and the desired quantity of the sample. It is contemplated that various lancet tips may be construted for use with the laser lancet, each tip being dedicated to a particular site and incision size. In a preferred embodiment, the lancets may be coded such as by color coding to identify a particular use.

DETAILED DESCRIPTION

Figure 1:
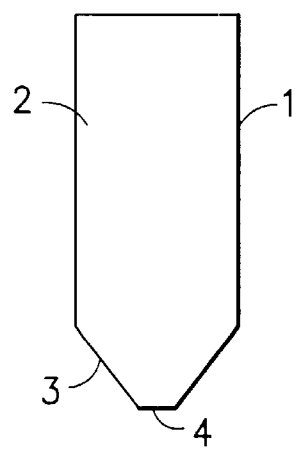
FIG. 1 is a schematic representation of a typical laser lancet used in blood sampling.

FIG. 1 shows schematically a typical laser lancet 1 used in the collection of blood samples. Laser lancet 1 includes laser body 2 having a narrow end forming a probe 3. Probe 3 defines an emitting end 4. Emitting end 4 includes a window through which a laser pulse is transmitted. Laser lancet 1 used in accordance with the present invention is a conventional laser such as the type used in medical applications for taking blood samples.

Figure 2:
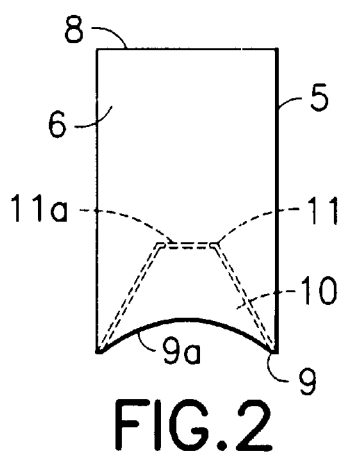
FIG. 2 shows the laser lancet tip of the present invention.

FIG. 2 illustrates one embodiment of a laser lancet tip 5 of the present invention. Lancet tip 5 includes an elongated housing 6 having an open proximal end 8 and an opposed specifically configured distal end 9. The housing 6 can be of any shape which may be readily adapted for use with laser lancet 1. The tip is constructed to be easily removably attached to the probe 3 of laser lancet 1 as shown in FIG. 3.

Figure 3:
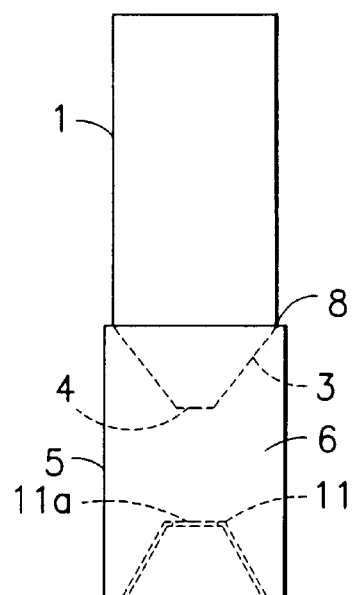
FIG. 3 shows the laser lancet tip of FIG. 2, affixed to the laser lancet of FIG. 1.

FIG. 3 illustrates laser lancet tip 5 attached to laser lancet 1. Laser lancet probe 3 is inserted into housing 6 until laser lancet probe 3 and housing 6 are frictionally engaged. The laser lancet tip 5 is thereby removably affixed to the laser lancet 1. Distal end 9 of housing 6 is shaped in the present embodiment to match the contour of an adult finger. In preferred embodiments lancet tips 5 would be formed to have distal ends 9 in various shapes to match the contours of body parts from which blood samples are taken.

Preferably, the housing of the laser lancet tip 5 is disposable and is made of conventional injection molded plastic. The laser lancet tip 5 would not pose the same threat to medical workers and patients as the needles and pointed blades and is designed for easy disposal. While a disposable laser lancet tip 5 is preferable, it is contemplated that lancet tip 5 may also be reusable as long as the tip could be sterilized sufficiently.

Inside housing 6 and extending from distal end 9 towards proximal end 8 is a recessed hollow frustroconical member 10. The truncated end of frustroconical member 10 has flat top 11. The wider distal end 9 of the frustroconical member defines an aperture 9a through which access to the collection site is provided. Flat top 11 includes an opening 11a therethrough optically aligned between the aperture 9a in distal end 9 and emitting end 4 of the laser so that the laser beam passes through the opening 11a. The laser beam would travel from the emitting end 4 of laser lancet 1 down the housing 6 from proximal end 8 through the opening 11a in flat top 11 and then through the aperture in distal end 9 to the surface of the skin. Aperture 9a defines an enclosed area which confines the cross section of the laser beam so that only a predetermined area of the site is incised. Thus by selective construction of aperture 9a of tip 5 so as to uniquely conform to a given site, the lancet tip provides a selected predetermined incision expanse at the site. As will be described in further detail, an optical filter such as a lens or other filter structure can be placed on or across flat top 11 to intensify or diminish the laser beam and thereby control the depth of the puncture to further define the puncture expanse.

While aperture 9a can take the form of an open recess in distal end 9 of tip 5, the aperture 9a can also be manufactured using a blocking material suitable for inhibiting the transmission of radiation at the wavelength of interest. The transmissive portion of the aperture can be clear glass or a physical hole through the blocking material. The aperture can be of any shape as long as it is capable of limiting the incident target area by masking the laser pulse.

Figure 4:
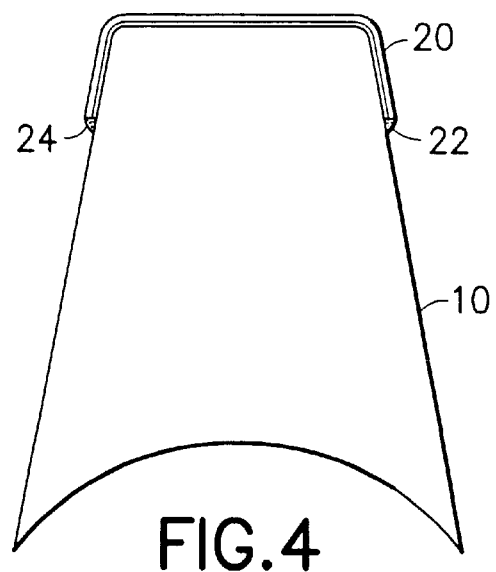
FIG. 4 is an enlarged showing of the interior structure of the laser lancet tip of FIG. 2.

Referring additionally to FIG. 4, a filter or lens 20 is shown positioned over the flat top 11 of frustroconical member 10. As mentioned above, the filter or lens 20 may be used to intensify or diminish the laser beam. The lens 20 could be a concave or convex lens of any material known in the art. A concave lens would be used to increase the depth of the puncture. The laser beam would pass through the lens 20 and the beam would converge. The converging beam would be smaller and, therefore, a greater percentage of the laser beam could fit through the aperture 9a and contact the skin. A convex lens would operate in the opposite manner. The laser beam would diverge after passing through the convex lens. A greater percentage of the diverging laser beam would be masked by the aperture and the puncture depth would be decreased.

A filter, on the other hand, would not alter the size of the laser beam but would instead absorb a percentage of the laser beam to control the puncture depth. The partially absorbed laser beam would continue on from the filter and eventually be masked by the aperture. The filter can be made from any suitable material known in the art.

The filter or lens 20, in a preferred embodiment, would be in the form of a sheet which could be stretched across flat top 11. The filter or lens sheets could also be varied in thickness to supply a variety of different puncture depths. As shown in FIG. 4, the filter or lens 20 may be secured to the flat top 11 of frustroconical member 10 by adhesive 22, 24.

Figure 5:
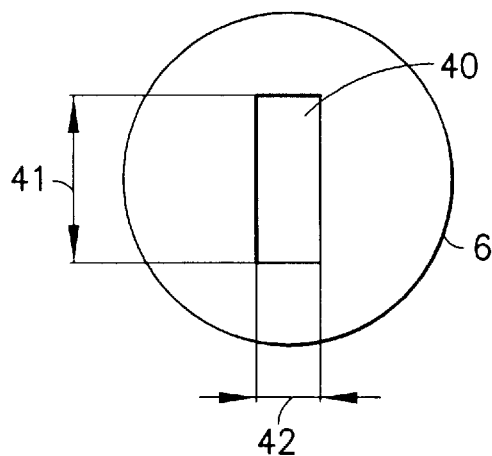
FIG. 5 is a bottom plan view of a fixed size aperture in the distal end of the laser lancet tip.

FIG. 5 illustrates a slit aperture 40 in distal end 9 of cylindrically shaped housing 6. Slit aperture 40 is defined by length 41 and width 42. In a preferred embodiment, slit aperture 40 is available in a variety of different lengths 41 or widths 42 in order to vary the target surface area upon which the laser pulse is incident.

When large blood samples are required from infants, the longest length 41 and width 42 would be used. If a small blood sample was needed or the patient was an adult, length 41 and width 42 would be reduced to provide the proper size incision.

Figure 6:
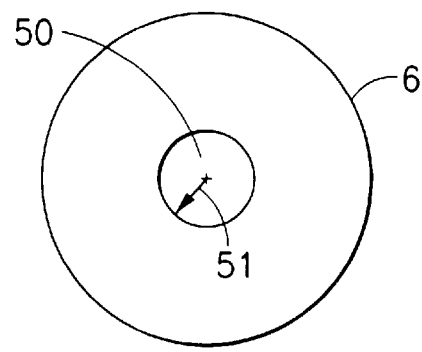
FIG. 6 is a bottom plan view of another embodiment of the fixed size aperture in the distal end of the laser lancet tip.

FIG. 6 illustrates circular aperture 50 in distal end 9 of cylindrically shaped housing 6. Circular aperture 50 has a radius 51. To collect large amounts of blood from infant patients, radius 51 would be a maximum value. To collect small amounts of blood from an adult or infant, radius 51 would be reduced to a predetermined size.

The aperture can be any shape which can be used to mask the laser pulse and can be varied in length or width to allow for different size incisions.

Figure 7:
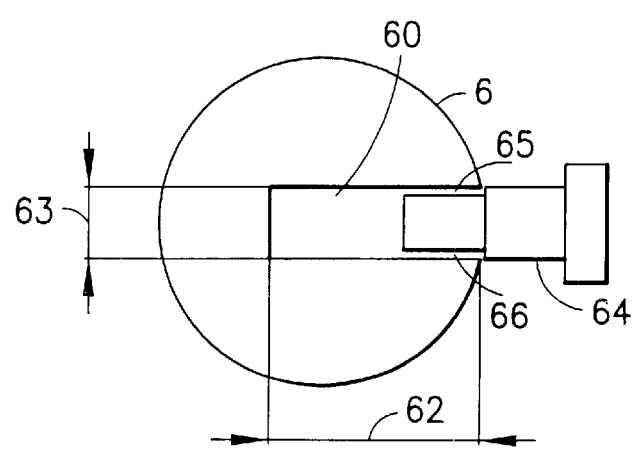
FIG. 7 is a bottom plan view of an embodiment of a variable size aperture in the distal end of the laser lancet tip.

FIG. 7 illustrates variable size aperture 60 in distal end 9 of cylindrically shaped housing 6. The area of variable size aperture 60 is defined by length 62 and width 63. Length 62 is increased or decreased by sliding tongue 64 along grooves 65, 66. Tongue 64 can be marked to make selection of specific size aperture easier.

The area of the variable size aperture 60 can be changed by any means known in the art and is not limited to the configuration depicted in FIG. 7.

The present invention thus provides a laser lancet assembly where a particular lancet tip may be selected for use in blood collection at a specific site. A plurality of tips may be manufactured, where each tip is designed to be used with a specific site and for a specific amount of blood to be collected.

As an example, one tip may be designed for taking blood samples from an adult finger. The tip would have an opening in the flat top of the frustroconical member and/or include a lens or filter which would effect a laser incision to collect the desired amount of blood. Other tips would be constructed to adapt to other sites and collection amounts. These tips can be coded such as by color coding to enable the medical technician to select the proper tip for each patient site.

Various changes and modifications can be made to the present invention. It is intended that all such changes and modifications come within the scope of the invention as set forth in the following claims.

What is claimed is:

1. A laser lancet assembly for controlling a blood collection incision comprising:

a laser lancet having a laser beam emitting end for effecting a blood collection incision; and a lancet tip selectively positioned over said laser beam emitting end of said laser lancet, said lancet tip including an elongated housing having an adjustable housing aperture of size and shape to define a controllable pre-selected incision expanse, whereby said adjustable aperture comprises an adjustable length, width, and radius.

2. The assembly of claim 1, wherein said distal end of said housing is shaped to match the contours of a body part.

3. The assembly of claim 2, wherein said housing includes identifying coding to code said tip to a particular use.

4. The assembly of claim 3 wherein said identifying coding includes color coding.

5. The assembly of claim 1, wherein said aperture of said lancet is a fixed size.

6. The assembly of claim 5, wherein said aperture of said lancet tip is rectangular and said aperture having a fixed length and width.

7. The assembly of claim 5, wherein said aperture of said lancet tip is circular, and said aperture having a fixed radius.

8. The assembly of claim 5, wherein said housing of said lancet tip is color coded according to said fixed size of said aperture.

9. A method for controlling a laser incision comprising the steps of:

providing a laser lancet for emitting an incision causing laser beam; and limiting the expanse of the emitted beam to define a predetermined incision expanse by providing a lancet tip over said laser lancet having an adjustable aperture thereon through which said laser beam may pass, said adjustable aperture being of size and shape to limit said incision expanse, whereby said adjustable aperture comprises an adjustable length, width, an radius.

10. A kit of parts for establishing a controlled laser incision comprising:

a laser lancet having a laser beam emitting end for effecting an incision; and a lancet tip adapted for attachment to said laser lancet, said lancet tip having an adjustable aperture of unique size and shape to define a distinct pre-selected incision expanse, whereby said adjustable aperture comprises an adjustable length, width, and radius.

11. The kit of claim 10, wherein said tip is color coded for unique identification.

* * * * *